US011724075B2

(12) United States Patent
Johnson (10) Patent No.: US 11,724,075 B2
(45) Date of Patent: Aug. 15, 2023

(54) DEPLOYMENT CONSTRAINING SHEATH THAT ENABLES STAGED DEPLOYMENT BY DEVICE SECTION

(71) Applicant: W. L. Gore & Associates, Inc., Newark, DE (US)

(72) Inventor: Matthew A. Johnson, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 147 days.

(21) Appl. No.: 15/955,381

(22) Filed: Apr. 17, 2018

(65) Prior Publication Data

US 2018/0296809 A1    Oct. 18, 2018

Related U.S. Application Data

(60) Provisional application No. 62/486,744, filed on Apr. 18, 2017.

(51) Int. Cl.
*A61M 27/00* (2006.01)
*A61B 17/11* (2006.01)
*A61B 17/00* (2006.01)

(52) U.S. Cl.
CPC ....... *A61M 27/002* (2013.01); *A61B 17/1114* (2013.01); *A61B 2017/00292* (2013.01); *A61B 2017/00867* (2013.01); *A61B 2017/1139* (2013.01); *A61M 2210/1042* (2013.01); *A61M 2210/1075* (2013.01)

(58) Field of Classification Search
CPC ...... A61B 17/1114; A61B 2017/00292; A61B 2017/00867; A61B 2017/1139
See application file for complete search history.

(56) References Cited

U.S. PATENT DOCUMENTS

| | | |
|---|---|---|
| 3,818,511 A | 6/1974 | Goldberg et al. |
| 4,119,100 A | 10/1978 | Rickett |
| 4,338,937 A | 7/1982 | Lerman |
| 4,381,765 A | 5/1983 | Burton |
| 5,224,953 A | 7/1993 | Morgentaler |
| 5,261,898 A | 11/1993 | Polin et al. |
| 5,354,308 A | 10/1994 | Simon et al. |
| 5,562,728 A | 10/1996 | Lazarus et al. |

(Continued)

FOREIGN PATENT DOCUMENTS

| | | |
|---|---|---|
| CN | 101374477 A | 2/2009 |
| CN | 101951983 A | 1/2011 |

(Continued)

OTHER PUBLICATIONS

International Search Report and Written Opinion from PCT/US2018/028120, dated Aug. 21, 2018, 17 pages.

(Continued)

*Primary Examiner* — Timothy J Neal
*Assistant Examiner* — Andrew P. Restaino (57) ABSTRACT

Various aspects of the present disclosure are directed toward medical devices, systems, and methods. The medical devices may include a portion having a radially expansive force greater than a radially expansive force other portions of the device. In addition, the medical device may include one or more constraining mechanisms for deployment of the medical devices.

19 Claims, 7 Drawing Sheets

(56) References Cited

U.S. PATENT DOCUMENTS

| | | |
|---|---|---|
| 5,741,297 A | 4/1998 | Simon |
| 5,755,778 A | 5/1998 | Kleshinski |
| 5,797,933 A | 8/1998 | Snow et al. |
| 5,830,222 A | 11/1998 | Makower |
| 5,868,783 A | 2/1999 | Tower |
| 5,945,994 A | 8/1999 | Shimizu et al. |
| 5,957,949 A | 9/1999 | Leonhardt et al. |
| 6,007,544 A | 12/1999 | Kim |
| 6,077,291 A | 6/2000 | Das |
| 6,120,534 A | 9/2000 | Ruiz |
| 6,165,209 A | 12/2000 | Patterson et al. |
| 6,168,621 B1 | 1/2001 | Vrba |
| 6,171,329 B1 | 1/2001 | Shaw et al. |
| 6,193,734 B1 | 2/2001 | Bolduc et al. |
| 6,214,029 B1 | 4/2001 | Thill et al. |
| 6,217,608 B1 | 4/2001 | Penn et al. |
| 6,290,728 B1 | 9/2001 | Phelps et al. |
| 6,315,708 B1 | 11/2001 | Salmon et al. |
| 6,315,792 B1 | 11/2001 | Armstrong et al. |
| 6,355,052 B1 | 3/2002 | Neuss et al. |
| 6,391,036 B1 | 5/2002 | Berg et al. |
| 6,391,039 B1 | 5/2002 | Nicholas et al. |
| 6,416,543 B1 | 7/2002 | Hilaire et al. |
| 6,419,681 B1 | 7/2002 | Vargas et al. |
| 6,432,127 B1 | 8/2002 | Kim et al. |
| 6,468,303 B1 | 10/2002 | Amplatz et al. |
| 6,485,496 B1 | 11/2002 | Suyker et al. |
| 6,485,507 B1 | 11/2002 | Walak et al. |
| 6,488,702 B1 | 12/2002 | Besselink |
| 6,579,314 B1 | 6/2003 | Lombardi et al. |
| 6,585,758 B1 | 7/2003 | Chouinard et al. |
| 6,616,675 B1 | 9/2003 | Evard et al. |
| 6,629,992 B2 | 10/2003 | Bigus et al. |
| 6,666,883 B1 | 12/2003 | Seguin et al. |
| 6,712,836 B1 | 3/2004 | Berg et al. |
| 6,863,684 B2 | 3/2005 | Kim et al. |
| 6,866,674 B2 | 3/2005 | Galdonik et al. |
| 6,911,037 B2 | 6/2005 | Gainor et al. |
| 6,945,994 B2 | 9/2005 | Austin et al. |
| 6,958,037 B2 | 10/2005 | Ewers et al. |
| 7,022,131 B1 | 4/2006 | Derowe et al. |
| 7,025,777 B2 | 4/2006 | Moore |
| 7,029,482 B1 | 4/2006 | Vargas et al. |
| 7,037,344 B2 | 5/2006 | Kagan et al. |
| 7,115,136 B2 | 10/2006 | Park et al. |
| 7,182,771 B1 | 2/2007 | Houser et al. |
| 7,223,274 B2 | 5/2007 | Vargas et al. |
| 7,252,680 B2 | 8/2007 | Freitag |
| 7,303,569 B2 | 12/2007 | Yencho et al. |
| 7,431,729 B2 | 10/2008 | Chanduszko |
| 7,527,644 B2 | 5/2009 | Mangiardi et al. |
| 7,547,321 B2 | 6/2009 | Silvestri et al. |
| 7,585,306 B2 | 9/2009 | Abbott et al. |
| 7,608,086 B2 | 10/2009 | Tanaka et al. |
| 7,632,302 B2 | 12/2009 | Vreeman et al. |
| 7,780,686 B2 | 8/2010 | Park et al. |
| 7,828,814 B2 | 11/2010 | Brenneman et al. |
| 7,892,247 B2 | 2/2011 | Conston et al. |
| 7,901,430 B2 | 3/2011 | Matsuura et al. |
| 8,043,360 B2 | 10/2011 | McNamara et al. |
| 8,109,946 B2 | 2/2012 | Cahill et al. |
| 8,114,125 B2 | 2/2012 | Seibold et al. |
| 8,197,498 B2 | 6/2012 | Coleman et al. |
| 8,257,389 B2 | 9/2012 | Chanduszko et al. |
| 8,262,691 B2 | 9/2012 | McGuckin et al. |
| 8,343,088 B2 | 1/2013 | Bates et al. |
| 8,398,676 B2 | 3/2013 | Roorda et al. |
| 8,409,167 B2 | 4/2013 | Roschak |
| 8,425,539 B2 | 4/2013 | Binmoeller et al. |
| 8,430,934 B2 | 4/2013 | Das |
| 8,435,284 B2 | 5/2013 | Eidenschink et al. |
| 8,454,632 B2 | 6/2013 | Binmoeller et al. |
| 8,579,935 B2 | 11/2013 | Devries et al. |
| 8,641,747 B2 | 2/2014 | Brenneman et al. |
| 8,679,171 B2 | 3/2014 | Deem et al. |
| 8,728,155 B2 | 5/2014 | Montorfano et al. |
| 8,740,940 B2 | 6/2014 | Maahs et al. |
| 8,864,813 B2 | 10/2014 | Barr |
| 8,870,916 B2 | 10/2014 | Ewers et al. |
| 8,992,604 B2 | 3/2015 | Gross et al. |
| 9,597,204 B2 | 3/2017 | Benary et al. |
| 9,668,853 B2 | 6/2017 | Shin |
| 9,782,533 B2 | 10/2017 | Brenneman et al. |
| 9,993,251 B2 | 6/2018 | Todd et al. |
| 10,004,509 B2 | 6/2018 | Todd |
| 10,363,040 B2 | 7/2019 | Sambandam |
| 10,806,458 B2 | 10/2020 | Todd |
| 11,439,396 B2 | 9/2022 | Gore et al. |
| 2001/0021872 A1 | 9/2001 | Bailey et al. |
| 2001/0047180 A1 | 11/2001 | Grudem et al. |
| 2002/0082627 A1 | 6/2002 | Berg et al. |
| 2002/0099431 A1 | 7/2002 | Armstrong et al. |
| 2002/0099437 A1 | 7/2002 | Anson et al. |
| 2002/0161341 A1 | 10/2002 | Stinson |
| 2002/0169475 A1 | 11/2002 | Gainor et al. |
| 2002/0183787 A1 | 12/2002 | Wahr et al. |
| 2003/0028213 A1 | 2/2003 | Thill et al. |
| 2003/0032967 A1 | 2/2003 | Park et al. |
| 2003/0069533 A1 | 4/2003 | Kakutani et al. |
| 2003/0093096 A1 | 5/2003 | McGuckin et al. |
| 2003/0109893 A1 | 6/2003 | Margas et al. |
| 2003/0120292 A1 | 6/2003 | Park et al. |
| 2003/0139819 A1 | 7/2003 | Beer et al. |
| 2003/0144578 A1 | 7/2003 | Koster |
| 2003/0191482 A1 | 10/2003 | Suyker et al. |
| 2003/0225421 A1 | 12/2003 | Peavey et al. |
| 2004/0073242 A1 | 4/2004 | Chanduszko |
| 2004/0078053 A1 | 4/2004 | Berg et al. |
| 2004/0092977 A1 | 5/2004 | Vargas et al. |
| 2004/0098105 A1 | 5/2004 | Stinson et al. |
| 2004/0133236 A1 | 7/2004 | Chanduszko |
| 2004/0204755 A1 | 10/2004 | Robin |
| 2004/0211433 A1 | 10/2004 | Albright |
| 2005/0049675 A1 | 3/2005 | Wallace |
| 2005/0055082 A1 | 3/2005 | Ben Muvhar et al. |
| 2005/0070934 A1 | 3/2005 | Tanaka et al. |
| 2005/0070935 A1 | 3/2005 | Ortiz |
| 2005/0070957 A1 | 3/2005 | Das |
| 2005/0149071 A1 | 7/2005 | Abbott et al. |
| 2005/0154465 A1 | 7/2005 | Hodges et al. |
| 2005/0228413 A1 | 10/2005 | Binmoeller et al. |
| 2005/0234509 A1 | 10/2005 | Widomski et al. |
| 2005/0251201 A1 | 11/2005 | Roue et al. |
| 2005/0273124 A1 | 12/2005 | Chanduszko |
| 2005/0288786 A1 | 12/2005 | Chanduszko |
| 2006/0047337 A1 | 3/2006 | Brenneman |
| 2006/0052821 A1 | 3/2006 | Abbott et al. |
| 2006/0106418 A1 | 5/2006 | Seibold et al. |
| 2006/0200228 A1 | 9/2006 | Penn et al. |
| 2006/0217761 A1 | 9/2006 | Opolski |
| 2007/0055358 A1 | 3/2007 | Krolik et al. |
| 2007/0073337 A1 | 3/2007 | Abbott et al. |
| 2007/0123917 A1 | 5/2007 | Ortiz et al. |
| 2007/0168014 A1* | 7/2007 | Jimenez ............... A61F 2/966 623/1.12 |
| 2007/0244518 A1 | 10/2007 | Callaghan |
| 2007/0249985 A1 | 10/2007 | Brenneman et al. |
| 2007/0282430 A1 | 12/2007 | Thommen et al. |
| 2007/0283552 A1 | 12/2007 | Gale et al. |
| 2008/0086168 A1 | 4/2008 | Cahill |
| 2008/0091235 A1 | 4/2008 | Sirota |
| 2008/0243151 A1 | 10/2008 | Binmoeller |
| 2008/0262518 A1 | 10/2008 | Freudenthal |
| 2009/0076541 A1 | 3/2009 | Chin et al. |
| 2009/0090366 A1 | 4/2009 | Cuevas et al. |
| 2009/0093873 A1 | 4/2009 | Navia |
| 2009/0118745 A1 | 5/2009 | Paul, Jr. |
| 2009/0143713 A1 | 6/2009 | Van Dam |
| 2009/0187240 A1 | 7/2009 | Clerc et al. |
| 2009/0228038 A1 | 9/2009 | Amin |
| 2009/0281557 A1 | 11/2009 | Sander et al. |
| 2010/0010520 A1 | 1/2010 | Takahashi et al. |
| 2010/0023132 A1 | 1/2010 | Imran |
| 2010/0036401 A1 | 2/2010 | Navia |

(56) References Cited

U.S. PATENT DOCUMENTS

| | | |
|---|---|---|
| 2010/0100105 A1 | 4/2010 | Bates et al. |
| 2010/0106171 A1 | 4/2010 | Arepally et al. |
| 2010/0114128 A1 | 5/2010 | Coleman et al. |
| 2010/0114290 A1* | 5/2010 | Rasmussen ............... A61F 2/95 623/1.11 |
| 2010/0130995 A1 | 5/2010 | Yevzlin |
| 2010/0174253 A1 | 7/2010 | Cline et al. |
| 2010/0234878 A1 | 9/2010 | Hruska et al. |
| 2010/0268316 A1 | 10/2010 | Brenneman et al. |
| 2010/0305590 A1 | 12/2010 | Holmes et al. |
| 2011/0040366 A1 | 2/2011 | Goetz et al. |
| 2011/0054381 A1 | 3/2011 | Van Dam et al. |
| 2011/0060398 A1 | 3/2011 | Tupil et al. |
| 2011/0118765 A1 | 5/2011 | Aguirre |
| 2011/0125244 A1* | 5/2011 | Roeder ................... A61F 2/966 623/1.11 |
| 2011/0137410 A1 | 6/2011 | Hacohen |
| 2011/0213415 A1 | 9/2011 | McGuckin et al. |
| 2011/0218609 A1* | 9/2011 | Chobotov ............... A61F 2/06 623/1.11 |
| 2011/0257461 A1 | 10/2011 | Lipperman et al. |
| 2011/0257723 A1 | 10/2011 | McNamara |
| 2011/0301689 A1* | 12/2011 | Dorn ......................... A61F 2/97 623/1.12 |
| 2012/0065652 A1 | 3/2012 | Cully et al. |
| 2012/0089216 A1 | 4/2012 | Rapaport et al. |
| 2012/0130417 A1 | 5/2012 | Lepulu et al. |
| 2012/0172927 A1 | 7/2012 | Cambell et al. |
| 2012/0232505 A1 | 9/2012 | Eskaros et al. |
| 2012/0241503 A1 | 9/2012 | Baxter, III et al. |
| 2013/0012969 A1 | 1/2013 | Shin |
| 2013/0030351 A1* | 1/2013 | Belhe ..................... A61F 5/0076 604/9 |
| 2013/0030521 A1 | 1/2013 | Nitzan et al. |
| 2013/0041451 A1 | 2/2013 | Patterson et al. |
| 2013/0053784 A1 | 2/2013 | Houser et al. |
| 2013/0096606 A1* | 4/2013 | Bruchman ............... A61F 2/013 606/200 |
| 2013/0165967 A1 | 6/2013 | Amin et al. |
| 2013/0197623 A1 | 8/2013 | McHugo |
| 2013/0218192 A1 | 8/2013 | Erzberger et al. |
| 2013/0245742 A1 | 9/2013 | Norris |
| 2013/0261531 A1* | 10/2013 | Gallagher ............. A61M 39/28 604/9 |
| 2013/0317546 A1 | 11/2013 | Brown |
| 2014/0012368 A1 | 1/2014 | Sugimoto et al. |
| 2014/0031842 A1 | 1/2014 | Brenneman et al. |
| 2014/0074155 A1 | 3/2014 | Rothstein |
| 2014/0236064 A1 | 8/2014 | Binmoeller et al. |
| 2014/0303710 A1 | 10/2014 | Zhang et al. |
| 2014/0343602 A1 | 11/2014 | Cox et al. |
| 2015/0005810 A1 | 1/2015 | Center |
| 2015/0066077 A1 | 3/2015 | Akpinar |
| 2015/0250630 A1* | 9/2015 | Irwin ....................... A61F 2/966 29/451 |
| 2015/0265437 A1* | 9/2015 | Fleury ..................... A61F 2/915 623/1.16 |
| 2015/0313595 A1 | 11/2015 | Houghton |
| 2015/0313598 A1 | 11/2015 | Todd et al. |
| 2015/0313599 A1 | 11/2015 | Johnson |
| 2016/0045199 A1 | 2/2016 | Mooney |
| 2016/0135813 A1* | 5/2016 | Johnson ............. A61B 17/0057 606/213 |
| 2016/0256169 A1* | 9/2016 | Ben-Muvhar .... A61B 17/12036 |
| 2017/0020498 A1 | 1/2017 | Blom |
| 2017/0105854 A1 | 4/2017 | Treacy et al. |
| 2018/0221194 A1 | 8/2018 | Eskaros et al. |
| 2018/0242972 A1 | 8/2018 | Todd |
| 2018/0250009 A1 | 9/2018 | Todd et al. |
| 2018/0296809 A1 | 10/2018 | Johnson |
| 2020/0015823 A1 | 1/2020 | Sambandam |
| 2020/0146680 A1 | 5/2020 | Houghton et al. |
| 2021/0085328 A1 | 3/2021 | Todd |
| 2022/0257252 A1 | 8/2022 | Gore et al. |
| 2022/0370071 A1 | 11/2022 | Johnson et al. |

FOREIGN PATENT DOCUMENTS

| | | |
|---|---|---|
| CN | 102395323 A | 3/2012 |
| CN | 103209649 A | 7/2013 |
| CN | 103598902 A | 2/2014 |
| CN | 104168839 A | 11/2014 |
| CN | 104244843 A | 12/2014 |
| CN | 104519838 A | 4/2015 |
| CN | 106413586 A | 2/2017 |
| DE | 10148185 A1 | 4/2003 |
| EP | 0991375 A1 | 4/2000 |
| EP | 1790297 | 5/2007 |
| EP | 1480565 B1 | 12/2008 |
| EP | 2543323 | 1/2013 |
| EP | 3136982 A2 | 3/2017 |
| EP | 3136984 A1 | 3/2017 |
| GB | 2409978 A | 7/2005 |
| JP | 2000-505316 A | 5/2000 |
| JP | 2001-501493 A | 2/2001 |
| JP | 2001520908 | 11/2001 |
| JP | 2001-340346 A | 12/2001 |
| JP | 2003-527939 A | 9/2003 |
| JP | 2004-049806 A | 2/2004 |
| JP | 2005-518863 A | 6/2005 |
| JP | 2005-528181 A | 9/2005 |
| JP | 2005-534390 A | 11/2005 |
| JP | 2006-006648 A | 1/2006 |
| JP | 2007-530128 A | 11/2007 |
| JP | 2009-508641 A | 3/2009 |
| JP | 2009518149 | 5/2009 |
| JP | 2010-523209 A | 7/2010 |
| JP | 2010-528821 A | 8/2010 |
| JP | 2011-509758 A | 3/2011 |
| JP | 2011-519709 A | 7/2011 |
| JP | 2013013715 | 1/2013 |
| JP | 2014-503246 A | 2/2014 |
| JP | 2015-500665 A | 1/2015 |
| JP | 2021-155586 A | 10/2021 |
| JP | 2021-192846 A | 12/2021 |
| WO | 97/27898 A1 | 8/1997 |
| WO | 97/32543 A1 | 9/1997 |
| WO | 98/02099 A1 | 1/1998 |
| WO | WO-199808462 | 3/1998 |
| WO | WO-199816174 A1 | 4/1998 |
| WO | 98/58600 A1 | 12/1998 |
| WO | WO-2001072367 A | 10/2001 |
| WO | 2003/028522 A2 | 4/2003 |
| WO | 03/73944 A1 | 9/2003 |
| WO | 2003/103476 A2 | 12/2003 |
| WO | 2004/012603 A2 | 2/2004 |
| WO | 2004/087236 A2 | 10/2004 |
| WO | 2005/089655 A1 | 9/2005 |
| WO | 2007/024964 A1 | 3/2007 |
| WO | 2007/053243 A2 | 5/2007 |
| WO | WO-2007100970 A2 | 9/2007 |
| WO | 2008/157172 A1 | 12/2008 |
| WO | 2009/082718 A1 | 7/2009 |
| WO | 2009/091899 A2 | 7/2009 |
| WO | 2009/109348 A1 | 9/2009 |
| WO | 2009/140195 A1 | 11/2009 |
| WO | 2009/146369 A1 | 12/2009 |
| WO | 2010/129162 A1 | 11/2010 |
| WO | 2012/034108 A1 | 3/2012 |
| WO | 2012/067912 A1 | 5/2012 |
| WO | WO-2012071075 A1 | 5/2012 |
| WO | WO-2013152891 A2 | 10/2013 |
| WO | 2015/168506 A1 | 11/2015 |
| WO | 2015/168507 A1 | 11/2015 |
| WO | 2015/168508 A2 | 11/2015 |

(56) References Cited

FOREIGN PATENT DOCUMENTS

WO    WO-2015168501 A2    11/2015
WO    WO-2015168504 A2    11/2015

OTHER PUBLICATIONS

International Preliminary Report on Patentability received for PCT Patent Application No. PCT/US15/28711, dated Nov. 17, 2016, 11 pages.
International Preliminary Report on Patentability received for PCT Patent Application No. PCT/US15/28715, dated Nov. 17, 2016, 8 pages.
International Preliminary Report on Patentability received for PCT Patent Application No. PCT/US15/28717, dated Nov. 17, 2016, 9 pages.
International Preliminary Report on Patentability received for PCT Patent Application No. PCT/US15/28721, dated Nov. 17, 2016, 8 pages.
International Search Report and Written Opinion from PCT/US2012/027984, dated Jun. 6, 2012, 11 pages.
International Search Report and Written Opinion from PCT/US2015/028707, dated Oct. 23, 2015, 19 pages.
International Search Report and Written Opinion from PCT/US2015/028721, dated Oct. 28, 2015, 13 pages.
International Search Report and Written Opinion received for PCT Patent Application No. PCT/US15/28711, dated Feb. 1, 2016, 17 pages.
International Search Report and Written Opinion received for PCT Patent Application No. PCT/US15/28715, dated Aug. 25, 2015, 12 pages.
International Search Report and Written Opinion received for PCT Patent Application No. PCT/US15/28717, dated Aug. 26, 2015, 13 pages.
European Search Report from 15721986.6 dated Dec. 12, 2017, 4 pages.
Extended European Search Report from EP18161679.8, dated Jun. 20, 2018, 7 pages.
International Search Report and Written Opinion from PCT/2015/028711, completed Jan. 20, 2016, 17 pages.
International Search Report and Written Opinion from PCT/US2015/028707, completed Oct. 14, 2015, 19 pages.
International Search Report for PCT/US2016/055255 dated Dec. 20, 2016 and mailed Jan. 20, 2017, 5 pages.

* cited by examiner

DEPLOYMENT CONSTRAINING SHEATH THAT ENABLES STAGED DEPLOYMENT BY DEVICE SECTION

CROSS-REFERENCE TO RELATED APPLICATION

This application claims the benefit of Provisional Application No. 62/486,744, filed Apr. 18, 2017, which is incorporated herein by reference in its entirety.

TECHNICAL FIELD

This disclosure relates generally to medical devices, and more specifically, to medical devices for connecting tissue layers to create an anastomosis, implantable devices for occluding inhibiting or preventing material movement through tissue apertures, sealing, and allowing healing of defects in tissues, and deployment of the medical devices discussed herein.

BACKGROUND

An anastomosis is a cross-connection between two tissue structures, such as blood vessels or intestines. For example, in the context of coronary artery bypass graft surgery, a graft vessel is anastomosed to a native coronary artery so that blood can flow through the graft vessel.

Anastomoses can be created in various manners including, but not limited to: end-to-end, end-to-side, and side-to-side anastomoses. Often, suturing is used to create such anastomoses.

SUMMARY

Various aspects of the present disclosure are directed toward medical device systems. The medical device systems may include an expandable medical device having a first end portion, a second end portion, and an intermediate portion between the first end portion and the second end portion. The intermediate portion of the expandable medical device may include a radially expansive force greater than a radially expansive force of at least one of the first end portion and the second end portion. In addition, the expandable medical device may include a first constraining mechanism configured to releasably constrain the expandable medical device, and a second constraining mechanism arranged between the expandable medical device and the first constraining mechanism and configured to lessen expansion of the intermediate portion of the expandable medical device in response to release of the first constraining mechanism.

Various aspects of the present disclosure are also directed toward systems for deploying a medical device having a first flange, a second flange, and an intermediate portion therebetween and a delivery configuration and a deployed configuration. The systems include a first constraining mechanism configured to constrain the expandable medical device to the delivery configuration and deploy the first flange and the second flange to the deployed configuration in response to release thereof, and a second constraining mechanism arranged between the expandable medical device and the first constraining mechanism and configured to maintain the intermediate portion of the expandable medical device in an intermediate configuration in response to release of the first constraining mechanism.

Aspects of the disclosure are also directed toward methods of deploying an expandable medical device having a delivery configuration and a deployed configuration. The methods include positioning the expandable medical device at the target location (with expandable medical device including a first end portion, a second end portion, and an intermediate portion having a radially expansive force greater than a radially expansive force of the first end portion). The methods also include releasing a first constraining mechanism to deploy the first end portion and the second end portion to the deployed configuration and deploy the intermediate portion to an intermediate configuration. Further, the methods include releasing a second constraining mechanism to deploy the intermediate portion to the deployed configuration.

According to one example ("Example 1"), a medical device system includes an expandable medical device including a first end portion, a second end portion, and an intermediate portion therebetween, the intermediate portion having a radially expansive force greater than a radially expansive force of at least one of the first end portion and the second end portion; a first constraining mechanism configured to releasably constrain the expandable medical device; and a second constraining mechanism arranged between the expandable medical device and the first constraining mechanism and configured to lessen expansion of the intermediate portion of the expandable medical device in response to release of the first constraining mechanism.

According to another example ("Example 2") further to Example 1, the first constraining mechanism and the second constraining mechanism are configured to deploy the intermediate portion of the expandable medical device to an intermediate configuration and deploy the first end portion and the second end portion of the expandable medical device to a deployed configuration in response to release of the first constraining mechanism.

According to another example ("Example 3") further to Example 2, the second constraining mechanism is configured to release and deploy the intermediate portion of the expandable medical device to the deployed configuration.

According to another example ("Example 4") further to Example 3, the second constraining mechanism is configured to release in response to a force applied thereto.

According to another example ("Example 5") further to Example 4, the force is a radial force applied within the intermediate portion of the expandable medical device, and the second constraining mechanism is configured to remain coupled to the expandable medical device subsequent to the force being applied thereto.

According to another example ("Example 6") further to Example 1, the first end portion includes a first flange, the second end portion includes a second flange, and the intermediate portion includes a substantially cylindrical shape.

According to another example ("Example 7") further to Example 6, the expandable medical device includes a first inflection area between the first flange and the intermediate portion, a second inflection area between the second flange and the intermediate portion, and the second constraining mechanism is arranged between the first inflection area and the second inflection area.

According to another example ("Example 8") further to Example 1, the second constraining mechanism is coupled to the expandable medical device, and the first constraining mechanism is configured to deploy the expandable medical device and uncouple from the expandable medical device in response to tension applied to the first constraining mechanism.

According to another example ("Example 9") further to Example 1, the first constraining mechanism is configured to releasably constrain the expandable medical device to a substantially cylindrical delivery configuration.

According to another example ("Example 10") further to Example 9, the first constraining mechanism extends from a proximal end of the expandable medical device to a distal end of the expandable medical device and back toward a proximal end of the expandable medical device.

According to one example ("Example 11") a system for deploying a medical device having a first flange, a second flange, and an intermediate portion therebetween, a delivery configuration, and a deployed configuration. In Example 11, the system includes: a first constraining mechanism configured to constrain the medical device to the delivery configuration and deploy the first flange and the second flange to the deployed configuration in response to release of the first constraining mechanism; and a second constraining mechanism arranged between the medical device and the first constraining mechanism and configured to maintain the intermediate portion of the medical device in an intermediate configuration in response to release of the first constraining mechanism.

According to another example ("Example 12") further to Example 11, the intermediate portion includes a radially expansive force greater than a radially expansive force of at least one of the first flange and the second flange.

According to another example ("Example 13") further to Example 11, the second constraining mechanism is coupled to the medical device and secured to the intermediate portion.

According to another example ("Example 14") further to Example 11, the second constraining mechanism is arranged about a circumference of the intermediate portion of the medical device.

According to another example ("Example 15") further to Example 11, a diameter of the intermediate portion in the intermediate configuration is approximately between 40% to 80% less than a diameter of the intermediate portion in the deployed configuration.

According to another example ("Example 16") further to Example 11, the first constraining mechanism is configured to deploy the medical device and uncouple from the medical device in response to release of the first constraining mechanism.

According to one example ("Example 17"), a method of deploying an expandable medical device having a delivery configuration and a deployed configuration. In Example 17, the method includes positioning the expandable medical device at the target location, the expandable medical device including a first end portion, a second end portion, and an intermediate portion therebetween, the intermediate portion having a radially expansive force greater than a radially expansive force of the first end portion; releasing a first constraining mechanism to deploy the first end portion and the second end portion to the deployed configuration and deploy the intermediate portion to an intermediate configuration; and releasing a second constraining mechanism to deploy the intermediate portion to the deployed configuration.

According to another example ("Example 18") further to Example 17, releasing the second constraining mechanism includes applying a force to the second constraining mechanism to deploy the intermediate portion to the deployed configuration from the intermediate configuration.

According to another example ("Example 19") further to Example 17, a diameter of the intermediate portion in the intermediate configuration is approximately between 40% to 80% less than a diameter of the intermediate portion in the deployed configuration.

According to another example ("Example 20") further to Example 17, releasing the first constraining mechanism includes uncoupling the first constraining mechanism from the expandable medical device, and releasing the second constraining mechanism includes maintaining at least a portion of the second constraining mechanism attached to the intermediate portion of the expandable medical device.

According to one example ("Example 21") a medical device system includes an expandable medical device including a first end portion, a second end portion, and an intermediate portion therebetween, the intermediate portion having a radially expansive force greater than a radially expansive force of at least one of the first end portion and the second end portion; a first constraining mechanism configured to releasably constrain the expandable medical device; and a second constraining mechanism arranged between the expandable medical device and the first constraining mechanism and configured to lessen expansion of the intermediate portion of the expandable medical device in response to release of the first constraining mechanism.

According to another example ("Example 22") further to Example 21, the first constraining mechanism and the second constraining mechanism are configured to deploy the intermediate portion of the expandable medical device to an intermediate configuration and deploy the first end portion and the second end portion of the expandable medical device to a deployed configuration in response to release of the first constraining mechanism.

According to another example ("Example 23") further to any one of Examples 21-22, the second constraining mechanism is configured to release and deploy the intermediate portion of the expandable medical device to the deployed configuration.

According to another example ("Example 24") further to Example 23, the second constraining mechanism is configured to release in response to a force applied thereto.

According to another example ("Example 25") further to Example 24, the force is a radial force applied within the intermediate portion of the expandable medical device, and the second constraining mechanism is configured to remain coupled to the expandable medical device subsequent to the force being applied thereto.

According to another example ("Example 26") further to any one of Examples 21-25, the first end portion includes a first flange, the second end portion includes a second flange, and the intermediate portion includes a substantially cylindrical shape.

According to another example ("Example 27") further to Example 26, the expandable medical device includes a first inflection area between the first flange and the intermediate portion, a second inflection area between the second flange and the intermediate portion, and the second constraining mechanism is arranged between the first inflection area and the second inflection area.

According to another example ("Example 28") further to any one of Examples 21-27, the second constraining mechanism is coupled to the expandable medical device, and the first constraining mechanism is configured to deploy the expandable medical device and uncouple from the expandable medical device in response to tension applied to the first constraining mechanism.

According to another example ("Example 29") further to any one of Examples 21-28, the first constraining mechanism is configured to releasably constrain the expandable medical device to a substantially cylindrical delivery configuration.

According to another example ("Example 30") further to Example 29, the first constraining mechanism extends from a proximal end of the expandable medical device to a distal end of the expandable medical device and back toward a proximal end of the expandable medical device.

According to one example ("Example 31"), a system for deploying a medical device having a first flange, a second flange, and an intermediate portion therebetween, a delivery configuration, and a deployed configuration with the system including: a first constraining mechanism configured to constrain the medical device to the delivery configuration and deploy the first flange and the second flange to the deployed configuration in response to release of the first constraining mechanism; and a second constraining mechanism arranged between the medical device and the first constraining mechanism and configured to maintain the intermediate portion of the medical device in an intermediate configuration in response to release of the first constraining mechanism.

According to another example ("Example 32") further to Example 31, the intermediate portion includes a radially expansive force greater than a radially expansive force of at least one of the first flange and the second flange.

According to another example ("Example 33") further to any one of Examples 31-32, the second constraining mechanism is coupled to the medical device and secured to the intermediate portion.

According to another example ("Example 34") further to any one of Examples 31-33, the second constraining mechanism is arranged about a circumference of the intermediate portion of the medical device.

According to another example ("Example 35") further to any one of Examples 31-34, a diameter of the intermediate portion in the intermediate configuration is approximately between 40% to 80% less than a diameter of the intermediate portion in the deployed configuration.

According to another example ("Example 36") further to any one of Examples 31-35, the first constraining mechanism is configured to deploy the medical device and uncouple from the medical device in response to release of the first constraining mechanism.

According to one example ("Example 37"), a method of deploying an expandable medical device having a delivery configuration and a deployed configuration, the method including: positioning the expandable medical device at the target location, the expandable medical device including a first end portion, a second end portion, and an intermediate portion therebetween, the intermediate portion having a radially expansive force greater than a radially expansive force of the first end portion; releasing a first constraining mechanism to deploy the first end portion and the second end portion to the deployed configuration and deploy the intermediate portion to an intermediate configuration; and releasing a second constraining mechanism to deploy the intermediate portion to the deployed configuration.

According to another example ("Example 38") further to Example 37, releasing the second constraining mechanism includes applying a force to the second constraining mechanism to deploy the intermediate portion to the deployed configuration from the intermediate configuration.

According to another example ("Example 39") further to any one of Examples 37-38, a diameter of the intermediate portion in the intermediate configuration is approximately between 40% to 80% less than a diameter of the intermediate portion in the deployed configuration.

According to another example ("Example 40") further to any one of Examples 37-39, releasing the first constraining mechanism includes uncoupling the first constraining mechanism from the expandable medical device, and releasing the second constraining mechanism includes maintaining at least a portion of the second constraining mechanism attached to the intermediate portion of the expandable medical device.

DETAILED DESCRIPTION

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

Various aspects of the present disclosure are directed to medical devices for connecting tissue layers, for example, to circumvent a conduit or organ blockage, such as by creating a direct passage between tissue structures to create an anastomosis that facilitates material flow therebetween. The expandable medical devices may be endoscopically deployable or deliverable via a catheter and may be self-expanding to facilitate a secure connection between the tissue structures. The present disclosure discusses one or more constraining mechanisms that facilitate deployment of the expandable medical devices that facilitate delivery thereof and lessen misdeployment.

Figure 1:
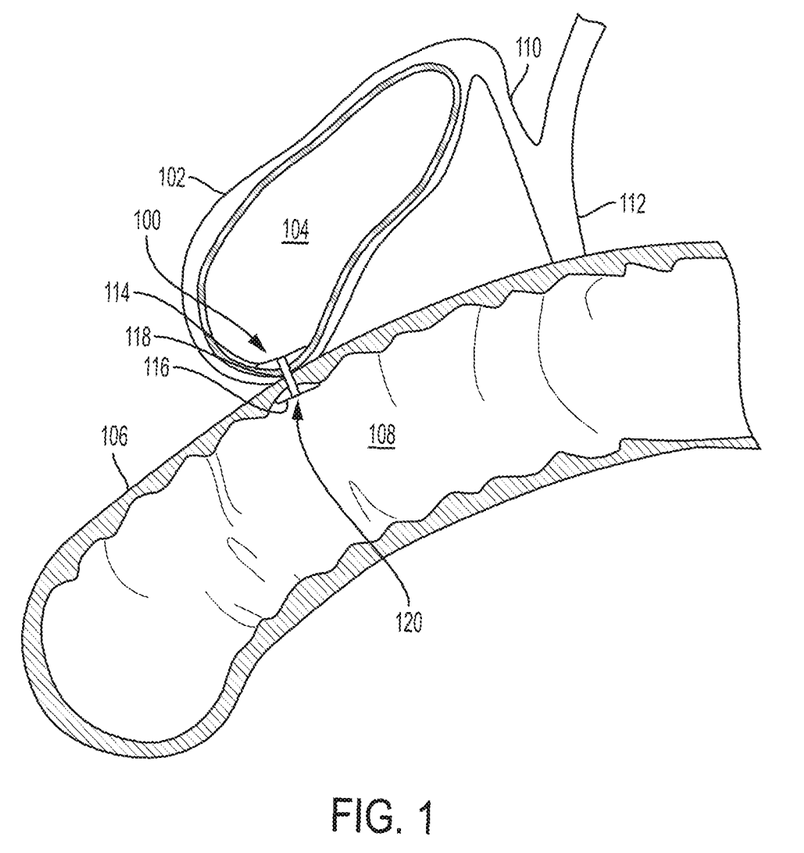
FIG. 1 shows a cutaway perspective view of an exemplary expandable medical device implanted within a patient, according to various aspects of the present disclosure.

FIG. 1 is a cutaway perspective view of an exemplary expandable medical device 100 implanted within a patient, according to various aspects of the present disclosure. The expandable medical device 100 is configured to be implanted in a patient to create a fluidic connection between spaces, tissue structures, conduits, organs, and the like, and combinations thereof. As shown in FIG. 1, for example, the expandable medical device 100 may be used to connect a gallbladder 102 (that defines an internal gallbladder space 104) with an intestine 106 (that defines an internal intestinal space 108). As a result, the expandable medical device 100 acts as a fluidic shunt device between the internal gallbladder space 104 and the internal intestinal space 108.

Such an implementation may provide a beneficial treatment to the patient when, for example, a flow blockage exists in the native anatomical conduits connecting the internal gallbladder space 104 and the internal intestinal space 108. In certain instances the patient may have one or more gallstones that cause a blockage of the patient's cystic duct 110 and/or common bile duct 112. In such a case, the expandable medical device 100 may provide a fluidic passageway such that bile from the gallbladder 102 may flow into the intestine 106.

The expandable medical device 100 may include a first end portion 114, a second end portion 116, and an intermediate portion 118 therebetween. The intermediate portion 118 defines a lumen 120 that extends longitudinally from the first end portion 114 to the second end portion 116. The lumen 120 may act as a connection (e.g., a shunt passageway) between the two spaces (e.g., tissue structures, conduits, organs) that the expandable medical device 100 connects. In the example shown in FIG. 1, the lumen 120 acts as a connection between the internal gallbladder space 104 and the internal intestinal space 108, such that the internal gallbladder space 104 is in fluid communication with the internal intestinal space 108 via the expandable medical device 100.

Although FIG. 1 shows the expandable medical device 100 connecting the gallbladder 102 and the intestine 106 of a patient, the expandable medical device 100 may be used in conjunction with various body tissue structures and organs such as, but not limited to, stomachs, colons, small intestines, pancreases, blood vessels, bladders, kidneys, and conduits.

Figure 2:
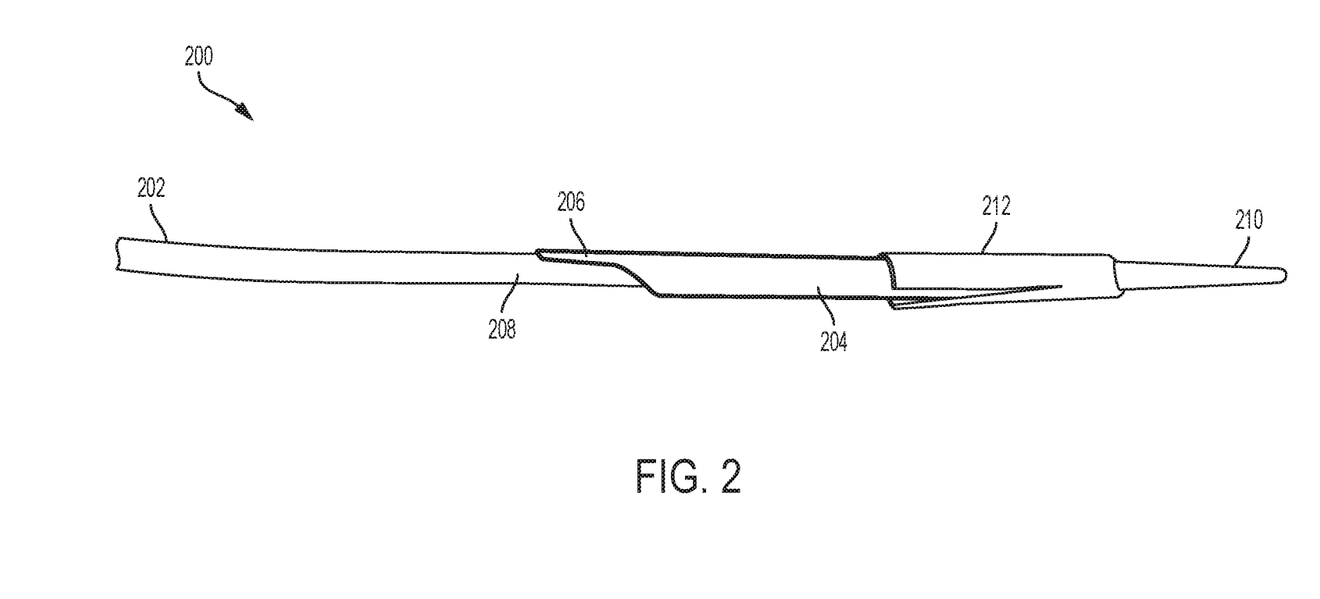
FIG. 2 shows a delivery system for an expandable medical device, according to various aspects of the present disclosure.

FIG. 2 shows a delivery system 200 for an expandable medical device, according to various aspects of the present disclosure. The delivery system 200 may include a catheter body 202 upon which the expandable medical device (not shown) may be arranged. The delivery system 200 also includes a first constraining mechanism 204 configured to constrain the expandable medical device to a delivery or constrain configuration. The first constraining mechanism 204 may be used in connection with a second constraining mechanism (as shown and discussed in further detail below with reference to FIGS. 3-6).

To deploy the expandable medical device arranged with the delivery system 200, tension may be applied to a deployment line 206 coupled to the first constraining mechanism 204. The deployment line 206 is accessible to a user such as a physician and may be arranged through a port 208 in the catheter body 202. In response to tension applied to the deployment line 206, the primary constraining mechanism 204 may open, withdraw or evert from an end of the delivery system 200, such as a distal tip 210, toward the port 208. In some embodiments, the first constraining mechanism 204 may have multiple layers constraining the expandable medical device and as such may move from one end of the delivery zone to the other end multiple times during deployment. In certain instances, the delivery system 200 may also include a skirt 212 that is arranged about the first constraining mechanism 204 prior to the delivery system 200 being traversed to a target location within a patient.

Figure 3:
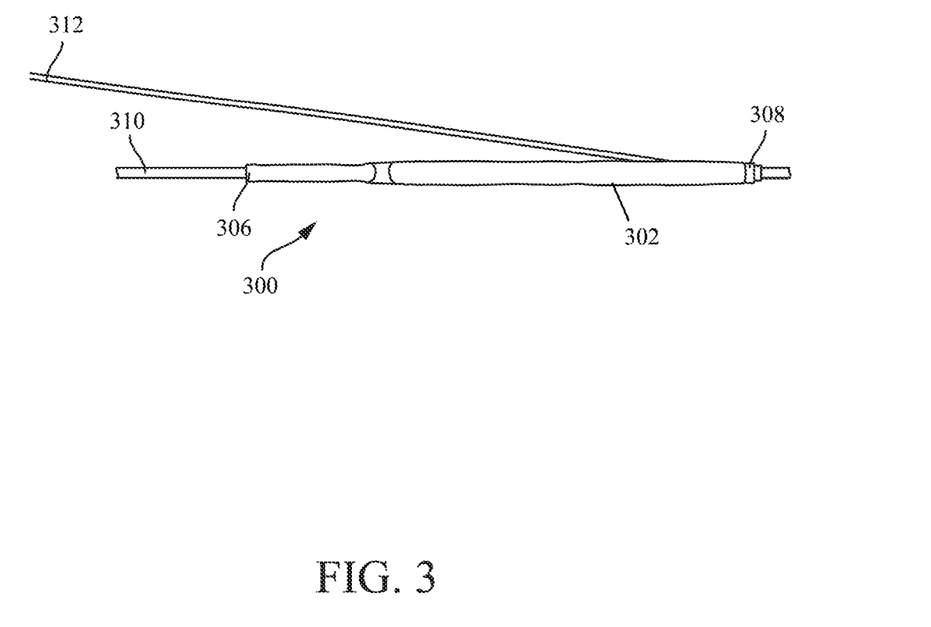
FIG. 3 shows an expandable medical device in a delivery configuration, according to various aspects of the present disclosure.

FIG. 3 shows an expandable medical device 300 in a delivery configuration, according to various aspects of the present disclosure. As shown in FIG. 3, a first constraining mechanism 302 is configured to constrain the expandable medical device 300 to the delivery configuration. The first constraining mechanism 302 extends between a proximal end 306 of the expandable medical device 300 to a distal end 308 of the expandable medical device 300. In addition, the expandable medical device 300 may be arranged on a delivery catheter or delivery system 310. The delivery catheter or delivery system 310, in certain instances, is routed within a patient to a target location for delivery of the expandable medical device 300.

To deploy the expandable medical device 300, tension may be applied to a deployment line 312 coupled to the first constraining mechanism 302, which is accessible to a user such as a physician. In response, the first constraining mechanism 302 may open, withdraw or evert from the proximal end 306 towards the distal end 308 and then continue back toward the proximal end 306 of the expandable medical device 300. Releasing the first constraining mechanism 302 in this manner may deploy the distal end 308 of the expandable medical device 300 prior to deploying the remaining portions of the expandable medical device 300.

Figure 4:
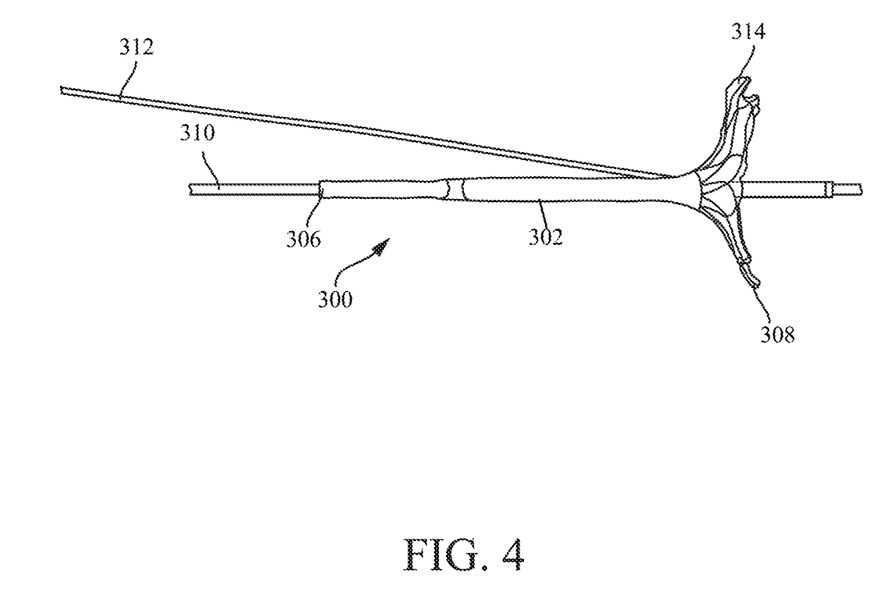
FIG. 4 shows the expandable medical device, shown in FIG. 3, in a step of a delivery, according to various aspects of the present disclosure.

FIG. 4 shows the expandable medical device 300 after deployment of the distal end 308 of the expandable medical device 300. As shown therein, the expandable medical device 300 may include a first flange 314 arranged at the distal end 308. The first flange 314 may be deployed after the first constraining mechanism 302 is withdrawn past the first flange. The user may continue to apply tension to the deployment line 312 of the first constraining mechanism 302 to continue deployment of the expandable medical device 300.

Figure 5:
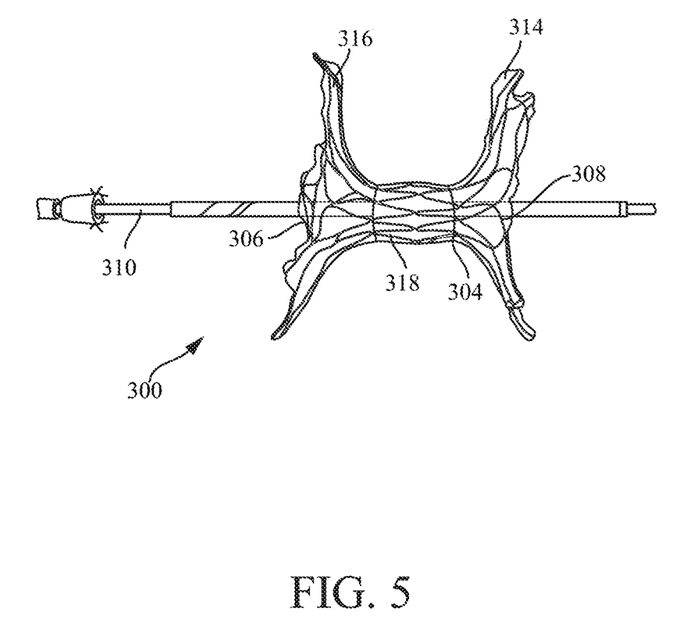
FIG. 5 shows the expandable medical device, shown in FIGS. 3 and 4, in another step of a delivery, according to various aspects of the present disclosure.

FIG. 5 shows the expandable medical device 300 after deployment of the proximal end 306 of the expandable medical device 300. As shown therein, the expandable medical device 300 may include a second flange 316 arranged at the proximal end 306. The first constraining mechanism 302 has been released past the proximal end 306 of the expandable medical device 300, and released and uncoupled from the expandable medical device 300. Thus, the first constraining mechanism 302 is configured to release and deploy the first flange 314 and the second flange 316 to a fully-deployed configuration in response to release thereof. An intermediate portion 318 of the expandable medical device 300, however, remains in an intermediate configuration as shown in FIG. 5.

A second constraining mechanism 304, arranged between the expandable medical device 300 and the first constraining mechanism 302 in the delivery configuration shown in FIGS. 2 and 3, is configured to maintain the intermediate portion 318 of the expandable medical device 300 in the intermediate configuration after the release of the first constraining mechanism 302. The intermediate portion 318 of the expandable medical device 300 may have a radially expansive force greater than a radially expansive force of one or both of the first flange 314 and the second flange 316 when they are constrained by the first constraining mechanism 302. As noted with reference to FIGS. 6A and B, for example, the expandable medical device 300 may include a plurality of elongate elements. The plurality of elongate elements may have a greater density and/or winding pattern in the intermediate portion 318 of the expandable medical device 300 than in one or both of the first flange 314 and the second flange 316. In addition and as a result, the intermediate portion 318 of the expandable medical device 300 has a greater resistance to compressive force (a greater radial strength) than one or both of the first flange 314 and the second flange 316.

In certain instances, the intermediate portion 318 is approximately cylindrical whereas the first flange 314 and the second flange 316 deploy approximately perpendicular to the intermediate portion 318 such that the expandable medical device 300 includes an hourglass shape having a lumen therethrough in an intermediate configuration (shown in FIG. 5). The second constraining mechanism 304 is coupled to the expandable medical device 300 and is secured to the intermediate portion 318. The second constraining mechanism 304 is arranged about a circumference of the intermediate portion 318 of the expandable medical device 300.

To facilitate staged deployment of the expandable medical device 300, the second constraining mechanism 304 may be configured to mitigate against premature expansion of the intermediate portion 318. The expandable medical device 300, in certain instances, is self-expanding and therefore is biased to deploy to the full-deployed configuration from the delivery configuration. In certain instances, the intermediate portion 318 and the first flange 314 and/or the second flange 316 having different radial forces may result in forces from the intermediate portion 318, desiring to be in the deployed configuration, to force the first constraining mechanism 302 from the expandable medical device 300. The second constraining mechanism 304 is configured to lessen expansion of the intermediate portion 318 by deploying the intermediate portion 318 to the intermediate configuration as opposed to directly to the deployed configuration.

The second constraining mechanism 304 is configured to release in response to a force applied thereto. In certain instances, the force is applied from within the intermediate portion 318 of the expandable medical device 300 to break, fracture, or distend the second constraining mechanism 304. In certain instances, the second constraining mechanism 304 remains coupled to the intermediate portion 318 of the expandable medical device 300 after release thereof. The intermediate portion 318 of the expandable medical device 300 may deploy to the fully-deployed configuration, for example, as shown in FIG. 6B, after release of the second constraining mechanism 304.

Figure 6A:
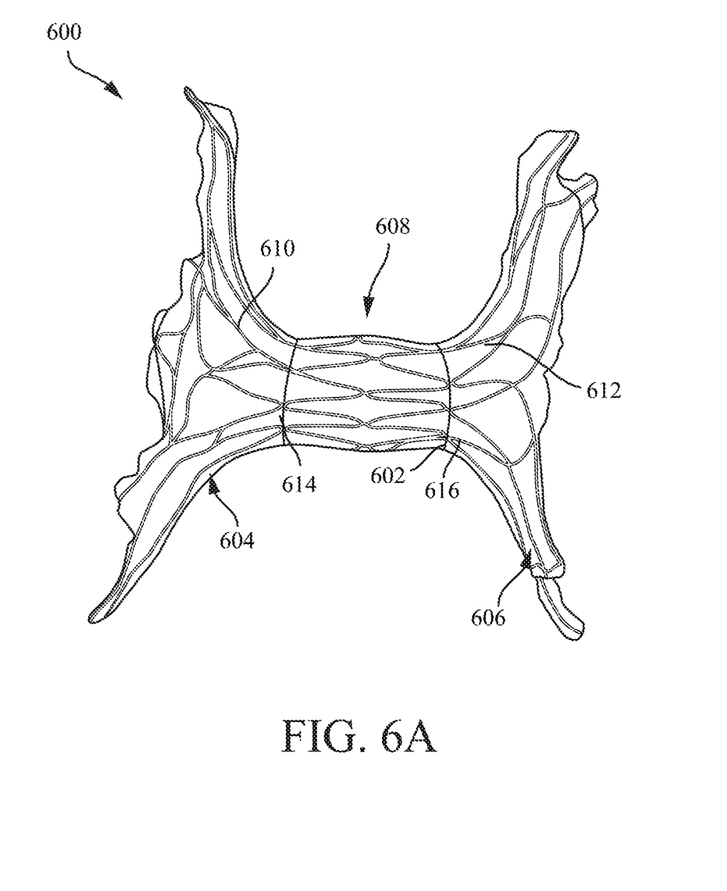
FIG. 6A shows an expandable medical device and constraining mechanism in an intermediate configuration, according to various aspects of the present disclosure.
Figure 6B:
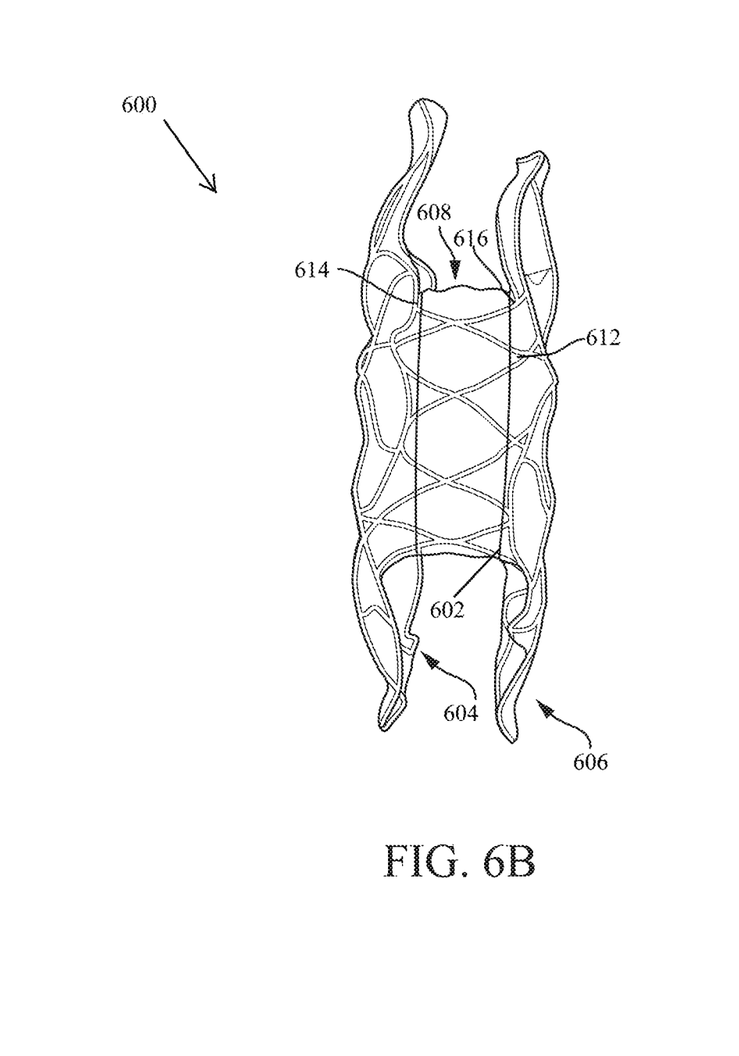
FIG. 6B shows the expandable medical device, shown in FIG. 6A, in a fully deployed configuration, according to various aspects of the present disclosure.

FIG. 6A shows an expandable medical device 600 and constraining mechanism 602, according to various aspects of the present disclosure, in an intermediate configuration. The expandable medical device 600 may include a first end portion 604 having a flange shape, a second end portion 606 having a flange shape, and an intermediate portion 608 extending therebetween.

In addition, the first end portion 604, the second end portion 606, and the intermediate portion 608 are formed by a framework of elongate elements 610. As shown in FIG. 6A, the elongate elements 610 in the intermediate portion 608 include a greater density than the first end portion 604 and the second end portion 606. The expandable medical device 600 may include a covering material 612 (which may also be referred to herein as a "covering"). In certain instances, the covering material 612 is disposed on some or all of the first end portion 604, the second end portion 606, and the intermediate portion 608. The elongate elements 610 in the intermediate portion 608 include a greater concentration or greater windings than the first end portion 604 and the second end portion 606. Thus, the intermediate portion 608 has a greater resistance to radial forces than the first end portion 604 and the second end portion 606. In certain instances, the difference in density of the elongate elements 610 in the intermediate portion 608 and the first end portion 604 and the second end portion 606 causes the first end portion 604 and the second end portion 606 results in the intermediate portion 608 having a greater radial expansive force than the first end portion 604 and the second end portion 606.

In addition and in certain instances, the intermediate portion 608 includes a radially expansive force greater than a radially expansive force than one or both of the first end portion 604 and the second end portion 606 in the delivery (constrained) configuration. The expandable medical device 600 is deployed by releasing a first constraining mechanism (e.g., as shown in FIG. 3). A second constraining mechanism, such as the constraining mechanism 602 shown in FIG. 6A, may be configured to lessen expansion of the intermediate portion 608 of the expandable medical device 600 in response to release of the first constraining mechanism. In certain instances and as shown in FIG. 6A, the second constraining mechanism 602 may be arranged to extend across the intermediate portion 608 of the expandable medical device 600. In addition and as shown in FIG. 6A, the second constraining mechanism 602 is configured to deploy the intermediate portion 608 of the expandable medical device 600 to an intermediate configuration, between the delivery configuration (shown in FIGS. 2 and 3) and a fully-deployed configuration shown in FIG. 6B, in response to release of the first constraining mechanism.

In addition to deploying the intermediate portion 608 of the expandable medical device 600 to the intermediate configuration, the first end portion 604 and the second end portion 606 are deployed to the deployed configuration after release of the first constraining mechanism (e.g., as shown in FIGS. 3-5).

In the intermediate configuration, the intermediate portion 608 of the expandable medical device 600 may include a diameter less than a diameter of the intermediate portion 608 of the expandable medical device 600 in the deployed configuration. The diameter of the intermediate portion 608 in the intermediate configuration may be approximately between 40% to 80% less than a diameter of the intermediate portion 608 in the deployed configuration. The second constraining mechanism 602 may constrain the intermediate portion 608 in the intermediate configuration until the second constraining mechanism 602 is released. For example, the second constraining mechanism 602 is configured to release and deploy the intermediate portion 608 of the expandable medical device 600 to the fully deployed configuration. The second constraining mechanism 602 is released in response to a force applied thereto. In certain instances, the force may be a radial force applied within the intermediate portion 608 of the expandable medical device 600. In addition, the force may be applied by an inflatable balloon or other force applied from within the intermediate portion 608 of the expandable medical device 600.

The second constraining mechanism 602 may release, rupture, distend, or otherwise break in response to the force. Further, the second constraining mechanism 602 may be configured to remain coupled to the expandable medical device 600 subsequent to the force being applied thereto with the first constraining mechanism being configured to deploy the expandable medical device 600 and uncouple from the expandable medical device 600 in response thereto. The second constraining mechanism 602 may surround or enclose a circumference of the intermediate portion 608 of the expandable medical device 600. In addition, the second constraining mechanism 602 may be a flexible film (formed from, for example, polytetrafluoroethylene (ePTFE)) and attached (and remain attached to after release of the first constraining mechanism) to one or more portions of the intermediate portion 608 of the expandable medical device 600 via a medical adhesive (e.g., fluorinated ethylene propylene (FEP), a polymer of tetrafluoroethylene, hexafluoropropylene and vinylidene fluoride (THV), and other biocompatible adhesives).

As noted above, the intermediate portion 608 includes a radially expansive force that is greater than a radially expansive force than one or both of the first end portion 604 and the second end portion 606 in the constrained (delivery) configuration. Thus, the second constraining mechanism 602 may be configured to mitigate against premature deployment of the expandable medical device 600. The intermediate portion 608 has a radially expansive force greater than one or both of the first end portion 604 and the second end portion 606 that may force the first constraining mechanism (not shown) to be removed/released from the expandable medical device 600 without a user applying tension to remove the first constraining mechanism. The second constraining mechanism 602 may be configured to lessen expansion of the intermediate portion 608, thereby mitigating against the potential for the intermediate portion 608 to force the first constraining mechanism from the expandable medical device 600 without the user removing the first constraining mechanism.

In addition, the second constraining mechanism 602 may be arranged between the first constraining mechanism (prior to release thereof) and the intermediate portion 608 of the expandable medical device 600. Further, the second constraining mechanism 602 may be arranged within the bounds of the intermediate portion 608 of the expandable medical device 600 as shown in FIG. 5A. The expandable medical device 600 may include a first inflection area 614 between the first end portion 604 and the intermediate portion 608, and a second inflection area 616 between the second end portion 606 and the intermediate portion 608. The first inflection area 614 and the second inflection area 616 may transition the substantially cylindrical shape of the intermediate portion 608 to, respectively, the first end portion 604 and the second end portion 606. Further, the second constraining mechanism 602 may be arranged to extend between the first inflection area 614 and the second inflection area 616. The second constraining mechanism 602 extending between but not covering the first inflection area 614 and the second inflection area 616 may facilitate deployment of the first end portion 604 and the second end portion 606 by not interfering or encroaching on the first end portion 604 and the second end portion 606 while maintaining the staged deployment of each portion of the expandable medical device 600.

In certain instances, the intermediate portion 608 of the expandable medical device 600 is constructed to have a tailored radial strength by, for example, varying sine wave amplitude, angle, number of apices per row, number of rows, and/or wire diameter of the elongate elements 610 (or other similar constructions). In addition, the intermediate portion 608 of the expandable medical device 600 includes a radial strength to resist circumferential loading from the surrounding tissue. In certain instances, the radial strength of the intermediate portion 608 of the expandable medical device 600 facilitates remodeling of the tissue external to the intermediate portion 608 to become approximate in size to the outer diameter of the intermediate portion 608. When the expandable medical device 600 (and the other expandable medical devices discussed herein) is implanted to form an anastomosis, the radial strength of the intermediate portion 608 may provide resistance to the hoop force applied by the surrounding tissue. Thus, the expandable medical device 600 substantially maintains an open lumen at a desired dimension.

FIG. 6B shows the expandable medical device 600, shown in FIG. 6A, in a full deployed configuration, according to various aspects of the present disclosure. The intermediate portion 608 of the expandable medical device 600 is no longer constrained by the second constraining mechanism 602. Thus, the intermediate portion 608 is in the fully-deployed configuration. As shown in comparing FIG. 6A and FIG. 6B, the intermediate portion 608 expands to a greater diameter from the intermediate configuration. The second constraining mechanism 602, in certain instances, remains coupled to the intermediate portion 608 of the expandable medical device 600 after release of the constraining force.

The expandable medical devices, as discussed herein, may form a connection between two areas. The connection may also be referred to herein as a "shunt," "passageway," "shunt passageway," or "tunnel". In certain instances, the expandable medical devices discussed herein are configured to be removable after implantation. For example, the expandable medical devices may be implanted and remain in place until the gallbladder and/or its associated ducts are cleared of blockages, after which the device is removed. In another example, the expandable medical devices may remain implanted until the body grows a tissue-anastomosis around the device, and then the device is removed. In other instances, tissue ingrowth into and/or around the device permanently implants the expandable medical device, and the expandable medical device is not removed. The expandable medical devices discussed herein may provide an alternative treatment for patients who are not suitable candidates for other types of treatments (e.g., gallbladder removal surgery) and/or to avoid known complications of other types of treatments (e.g., external biliary drainage).

In certain instances, the elongate elements or framework of the expandable medical devices may be treated in various ways to increase the radiopacity of the expandable medical devices for enhanced radiographic visualization. In some embodiments, the expandable medical devices are at least partially a drawn-filled type of NiTi containing a different material at the core, such as a material with enhanced radiopacity. In some embodiments, the devices include a radiopaque cladding or plating on at least portions of the expandable medical devices. In certain instances, one or more radiopaque markers are attached to the expandable medical devices. In certain instances, the elongate elements and/or other portions of the expandable medical devices provided herein are also visible via ultrasound, and may include portions with enhanced echogenicity.

In addition, the covering material arranged on the expandable medical devices may be generally fluid impermeable. For example, the covering material may be made of a material that inhibits or reduces passage of blood, bile and/or other bodily fluids and materials through the covering material. In certain instances, the covering material has a material composition and configuration that inhibits or prevents tissue ingrowth and/or endothelialization or epithelialization into the covering material. In addition, the covering material may be configured to inhibit or prevent tissue ingrowth and/or endothelialization such that the expandable medical devices may be more readily removed from the patient at a future date. In certain instances, the covering material, or portions thereof, may include a microporous structure that provides a tissue ingrowth scaffold for durable sealing and/or supplemental anchoring strength of the expandable medical devices.

The covering material and the constraining mechanisms may include a fluoropolymer membrane, such as an expanded polytetrafluoroethylene (ePTFE) polymer, polyvinylidene fluoride (PVDF), or polyvinylidene acetate (PVDA). In other instances, the covering material comprises a polyester, a silicone, a urethane, biocompatible polymer(s), polyethylene terephthalate (e.g., Dacron®), bioabsorbable materials, copolymers, or combinations thereof. In addition, the covering material may include a bioabsorbable web. Expanded polytetrafluoroethylene (ePTFE) membranes prepared in accordance with the methods described in U.S. Pat. No. 7,306,729 to Bacino et al., U.S. Pat. No. 3,953,566 to Gore, U.S. Pat. No. 5,476,589 to Bacino, or U.S. Pat. No. 5,183,545 to Branca et al. may be used as the covering material herein. Additionally, expanded modified PTFE and expanded copolymers of PTFE, such as described in U.S. Pat. No. 5,708,044 to Branca; U.S. Pat. No. 6,541,589 to Baillie; U.S. Pat. No. 7,531,611 to Sabol et al.; U.S. Pat. No. 8,637,144 to Ford; and U.S. Pat. No. 9,139,669 to Xu et al. may be used herein. In other embodiments, the bioabsorbable material may also provide an anti-migration feature by promoting attachment between the expandable medical devices and tissue until the bioabsorbable material is absorbed.

The covering material (or portions thereof) may also be modified by one or more chemical or physical processes that enhance one or more properties of the coating. For example, a hydrophilic coating may be applied to the covering material to improve the wettability and echo translucency of the covering. In certain instances, the covering material, or portions thereof, may be modified with chemical moieties that facilitate one or more of endothelial cell attachment, endothelial cell migration, endothelial cell proliferation, and resistance to or promotion of thrombosis. In certain instances, the covering material, or portions thereof, may be modified to resist biofouling. In addition, the covering material, or portions thereof, may be modified with one or more covalently attached drug substances (e.g., heparin, antibiotics, and the like) or impregnated with the one or more drug substances. The drug substances can be released in situ to promote healing, reduce tissue inflammation, reduce or inhibit infections, and to promote various other therapeutic treatments and outcomes. In some embodiments, the drug substance may be, but is not limited to a corticosteroid, a human growth factor, an anti-mitotic agent, an antithrombotic agent, a stem cell material, or dexamethasone sodium phosphate. In addition, a pharmacological agent may be delivered separately from the covering material to the target site to promote tissue healing or tissue growth.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

What is claimed is:
1. A medical device system comprising:
   an expandable medical device including a first end portion defining a first flange, a second end portion defining a second flange, and an intermediate portion therebetween, the intermediate portion including a radially expansive force greater than a radially expansive force of one or both of the first flange and the second flange;
   a first constraining mechanism configured to releasably constrain the expandable medical device to a delivery diameter, the first constraining mechanism operable to evert, wherein the radially expansive force of the intermediate section of the expandable medical device is configured to facilitate forcing the first constraining mechanism from the expandable medical device,
   a deployment line coupled to the first constraining mechanism configured to withdraw or evert the first constraining mechanism in response to tension applied to an end of the deployment line; and
   a second constraining mechanism arranged between the expandable medical device and the first constraining mechanism and configured to lessen expansion of the intermediate portion of the expandable medical device to an intermediate diameter that is greater than the delivery diameter in response to release of the first constraining mechanism and deploy the intermediate portion to a deployed diameter greater than the intermediate diameter in response to rupture, distension, or breakage of the second constraining mechanism in response to a force and wherein the second constraining mechanism remains coupled to the expandable medical device subsequent to the force being applied thereto, after the expandable medical device is implanted, and removal of the deployment line from a body of a patient; and
   wherein the second constraining mechanism is a film and is coupled to the expandable medical device via an adhesive.

2. The system of claim 1, wherein the first constraining mechanism is configured to deploy the intermediate portion of the expandable medical device to an intermediate configuration and deploy the first end portion and the second end portion of the expandable medical device to a deployed configuration in response to release of the first constraining mechanism.

3. The system of claim 2, wherein the second constraining mechanism is configured to release and deploy the intermediate portion of the expandable medical device to the deployed configuration.

4. The system of claim 3, wherein the second constraining mechanism is coupled to the expandable medical device and configured to rupture in response to the force applied thereto.

5. The system of claim 4, wherein the force is a radial force applied within the intermediate portion of the expandable medical device, and the second constraining mechanism is configured to remain coupled to the expandable medical device subsequent to the force being applied thereto.

6. The system of claim 1, wherein the first end portion comprises the first flange, the second end portion comprises the second flange, and the intermediate portion comprises a substantially cylindrical shape.

7. The system of claim 6, wherein the expandable medical device comprises a first inflection area between the first flange and the intermediate portion, a second inflection area between the second flange and the intermediate portion, and the second constraining mechanism is arranged between the first inflection area and the second inflection area.

8. The system of claim 1, wherein the second constraining mechanism is coupled to the expandable medical device, and the first constraining mechanism is configured to deploy the expandable medical device and uncouple from the expandable medical device in response to tension applied to the first constraining mechanism.

9. The system of claim 1, wherein the first constraining mechanism is configured to releasably constrain the expandable medical device to a substantially cylindrical delivery configuration.

10. The medical device system of claim 1, wherein the first flange and the second flange have a diameter greater than a diameter of the intermediate portion of the expandable medical device when in a deployed configuration.

11. The medical device system of claim 1, wherein the first flange and the second flange are operable to deploy substantially perpendicular to the intermediate portion when released.

12. The medical device system of claim 1, wherein the first flange and the second flange has a radial force that is different than a radial force of the intermediate portion of the expandable medical device.

13. The medical device system of claim 1, wherein the expandable medical device is defined by a plurality of elongate elements, wherein the plurality of elongate elements includes a greater density of elongate elements at the intermediate portion.

14. A system for deploying a medical device having a first flange, a second flange, and an intermediate portion therebetween, a first inflection area between the first end portion and the intermediate portion, a second inflection area between the second end portion and the intermediate portion, a delivery configuration, and a deployed configuration, the system comprising:
   a first constraining mechanism configured to constrain the medical device to the delivery configuration and deploy the first flange and the second flange to the deployed configuration in response to release of the first constraining mechanism, the first constraining mechanism operable to evert;
   a deployment line coupled to the first constraining mechanism configured to withdraw or evert the first constraining mechanism in response to tension applied to an end of the deployment line; and
   a second constraining mechanism is a flexible film arranged between the medical device and the first constraining mechanism and positioned extending between the first inflection area and the second inflection area, the second constraining mechanism being configured to deploy the intermediate portion of the medical device to an intermediate diameter that is greater than a delivery diameter and maintain the intermediate portion of the medical device in an intermediate configuration in response to release of the first constraining mechanism and deploy the intermediate portion to a deployed diameter greater than the intermediate diameter in response to rupture, distension, or breakage of the second constraining mechanism in response to a force and remain coupled to the medical device subsequent to the force being applied thereto, after the expandable medical device is implanted, and removal of the deployment line from a body of a patient; and
   wherein the second constraining mechanism is coupled to the medical device via an adhesive.

15. The system of claim 14, wherein the second constraining mechanism is coupled to the medical device and secured to the intermediate portion.

16. The system of claim 14, wherein the second constraining mechanism is arranged about a circumference of the intermediate portion of the medical device.

17. The system of claim 14, wherein a diameter of the intermediate portion in the intermediate configuration is approximately between 40% to 80% less than a diameter of the intermediate portion in the deployed configuration.

18. The system of claim 14, wherein the first constraining mechanism is configured to deploy the medical device and uncouple from the medical device in response to release of the first constraining mechanism.

19. A medical device system comprising:
   an expandable shunt including a first end portion, a second end portion, and an intermediate portion therebetween, the intermediate portion being defined by a plurality of elongate elements, wherein the plurality of elongate elements includes a greater density of elongate elements at the intermediate portion;
   a first constraining mechanism configured to releasably constrain the expandable shunt to a delivery diameter, the first constraining mechanism operable to evert,
   a deployment line coupled to the first constraining mechanism configured to withdraw or evert the first constraining mechanism in response to tension applied to an end of the deployment line; and
   a second constraining mechanism arranged between the expandable shunt and the first constraining mechanism and configured to lessen expansion of the intermediate portion of the expandable shunt to an intermediate diameter that is greater than the delivery diameter in response to release of the first constraining mechanism and deploy the intermediate portion to a deployed diameter greater than the intermediate diameter in response to rupture, distension, or breakage of the second constraining mechanism in response to a force and wherein the second constraining mechanism remains coupled to the expandable shunt subsequent to the force being applied thereto and removal of the deployment line from a body of a patient; and
   wherein the second constraining mechanism is a film and is coupled to the expandable shunt via an adhesive.

* * * * *